(12) United States Patent
Shupe et al.

(10) Patent No.: US 6,290,964 B1
(45) Date of Patent: Sep. 18, 2001

(54) ANTIMICROBIAL AGENTS ISOLATED FROM ALOE VERA

(76) Inventors: Kathleen Shupe, 1845 East Northgate Dr., Irving, TX (US) 75062; Billy C. Coats, 4433 Crooked La., Dallas, TX (US) 75229

( * ) Notice: Subject to any disclaimer, the term of this patent is extended or adjusted under 35 U.S.C. 154(b) by 0 days.

(21) Appl. No.: 09/262,731

(22) Filed: Mar. 4, 1999

(Under 37 CFR 1.47)

Related U.S. Application Data

(60) Provisional application No. 60/077,145, filed on Mar. 6, 1998.

(51) Int. Cl.[7] .............................. A61K 65/00; C12Q 1/02; C12Q 1/18
(52) U.S. Cl. ........................ 424/195.1; 435/29; 435/32
(58) Field of Search ...................... 435/29, 32; 424/195.1

(56) References Cited

U.S. PATENT DOCUMENTS 5,356,811 * 10/1994 Coats .................................. 435/267
5,902,796 * 5/1999 Shand et al. ........................... 514/54

OTHER PUBLICATIONS

Levin et al. Phytotherapy Research. 1988. vol. 2, No. 2, pp. 67–69.*

Klein et al. Journal of American Academy of Dermatology. Apr. 1988. vol. 18, No. 4, part 1, pp. 714–720.*

* cited by examiner

*Primary Examiner*—Sandra E. Saucier
*Assistant Examiner*—Vera Afremova
(74) *Attorney, Agent, or Firm*—Edwin S. Flores; Matthew E. Burr; Gardere Wynne Sewell LLP

(57) ABSTRACT

Antimicrobial agents and method for isolation thereof from the gel liquid of *Aloe vera* includes at least one antimicrobial agent isolated from the clear gel isolated from the whole leaf of the *Aloe vera* plant, wherein the antimicrobial agent is an agent produced by the *Aloe vera* and/or indigenous bacteria that colonize the *Aloe vera* plant, is disclosed.

7 Claims, 1 Drawing Sheet

ANTIMICROBIAL AGENTS ISOLATED FROM ALOE VERA

This application claims the benefit under 35 U.S.C. §119(e) of U.S. provisional application Ser. No. 60/077,145, Filed Mar. 6, 1998.

TECHNICAL FIELD OF THE INVENTION

The present invention relates in general to the field of antimicrobial agents, and more particularly, to the characterization and isolation of agents that are responsible for antimicrobial activity of *Aloe vera* and its gel.

BACKGROUND OF THE INVENTION

Without limiting the scope of the invention, its background is described in connection with the identification of novel anti-microbial agents isolated from *Aloe vera*, as an example.

Heretofore, in this field, organisms that cause infectious disease, namely, viruses, bacteria, fungi and multicellular parasites, humankind has sought to control their morbidity and mortality. With the isolation and characterization of powerful antibiotics, beginning over half a century ago, the balance of power between humans and microbes has been shifted toward humankind. For several decades after the introduction of penicillin in the 1940's, for example, the conquest of infectious disease appeared imminent. The widespread use of antibiotics, added to the evolutionary flexibility of microbes, has made that victory less than certain.

An increasing number of bacteria, fungi and other microbes are developing resistance to antibiotics. A number of factors have contributed to the increase in microbes that are resistant to antimicrobial agents. The use of combinations of anti-microbial agents to treat nosocomial infections, particularly among patients whose immune systems are compromised by AIDS, chemotherapy, or immunosuppressive drugs, has led to a dramatic increase in multiple drug resistant (MDR) infections. Unfortunately, the future does not look bright in the war against infectious disease, as MDR strains of microbes continue to proceeding at an alarming rate. In fact, MDR strains are adapting faster than the introduction of new, more potent antibiotics.

Microbes have been developing strategies to cope with change for hundreds of millions of generations. In fact, some bacteria have generation cycles of 20 minutes, with each cycle providing the opportunity to evolve and adapt. Bacteria have adapted to an extraordinary range of conditions and developed defenses against all sorts of environmental threats, environmental and artificial. To a microbe the human body is just another environment to colonize. While antibiotics are just another toxic environmental agent against which the microbe must develop an escape strategy. For organisms with populations that have already adapted to such extreme environments as boiling underwater hot-springs, learning to cope and evade antibiotics was only a matter of time and evolution.

Overuse of antibiotics has contributed to the problem of MDR microbial strains. The indiscriminate use of antibiotics throughout the world contributes to the continued emergence of MDR strains of bacteria such as Pseudomonas, Streptococcus and Staphylococcus. MDR strains have evolved in large part because many patients fail to complete the required course of antibiotic treatment, allowing stronger members of the microbial pool to be selected for in the next round of treatment. Increases in ear and sinus infections in children have been caused by the use of antibiotics to treat viral infections, infections that are not susceptible to antibiotic treatment. The current trend in medicine is to prescribe second-line and even last-resort antibiotics in place of first-line antibiotics. Even when there is no reason to suspect resistance to first-line antibiotics, the drive toward using stronger, faster drugs is inevitable when faced with a sick patient. In the case of recurrent lung infections in cystic fibrosis patients, physicians have had no choice but to escalate to antibiotic treatment with second-line antibiotics, eventually causing the infecting bacteria to become resistant to all available antibiotics.

The emergence of MDR microbes has changed the balance between host and parasite, from a position in which the medical community seemed poised to achieve a conquest has lost ground in achieving a permanent conquest of microbial infection. But much has been learned in the process. Using a deeper understanding of microbes and their mechanisms of resistance, the biomedical community can continue to mount a broad array of defenses against them. The microbes growing resistance to traditional antibiotics has renewed the attention to medical basics, such as public health measures, that include a renewed effort to stem infectious diseases by increasing hygiene. For example, in HIV-infected populations, which have become breeding grounds for resistant microbes, renewed educational outreach efforts focus on the use of prophylactics.

Nosocomial infections present the greatest threat to immuno-compromised patients, because MDR microbes infect the most vulnerable patients. It is the increase in MDR of microbes, and in particular bacteria, that has led to a resurgence of interest in revitalizing and improving basic techniques (like hand-washing) for preventing the spread of infection. It has also increased the need for alternative, next-generation, anti-microbial agents. These anti-microbial agents, viz., anti-viral, anti-bacterial, anti-fungal and anti-parasitic, must also be safe for use in humans and other animals.

Antimicrobial-drug resistance is an increasingly important factor and poses a serious international challenge to public health in community and institutional settings. The list of resistant bacteria of major public health importance includes those causing tuberculosis, gonorrhea, pneumococcal infections, and hospital-acquired enterococcal and staphylococcal infections. Antimicrobial-drug resistance has resulted in prolonged and more serious illness, the use of more expensive and often more toxic drugs and drug combinations, and increased fatality rates.

While pharmaceutical and biotechnology companies are constantly developing novel products based on presently known antibiotics to overcome resistance, the next-generation of anti-microbial agents must break from the known approaches to isolate and characterize these activities. A better understanding of the microbiology and molecular genetics of microbial resistance is leading to the development of a new generation of anti-microbial agents that use an approach that is intended to attack standard mechanisms of action to kill bacteria or fungi. These so called new approaches to fighting microbial infections rely on variations of existing drugs having longer half-lives and more potent effects, but rely on the existing database of pharmaceutics to attempt to outpace the microbes ability to evolve.

SUMMARY OF THE INVENTION

Both competition for nutrients and bacteriocin production play a role in determining the establishment of microbial communities in nature. When analyzing symbiotic associations this may be further influenced by the presence of antimicrobial chemicals produced by the host. In the case of *Aloe vera barbedensis,* the plant has been shown for centuries to exert broad spectrum healing activities. The source of the antimicrobial agents isolated herein were determined, as were the distinct populations of bacteria, and their dynamics within the indigenous microflora of *Aloe vera.* Localization of specific microbial populations was assessed using both direct culture of dissected plant material and immunological detection within tissue sections. Relative size and population diversity were determined through direct culture. Immunological detection demonstrated discrete populations within specific plant structures.

Bacterial identification was accomplished using standard staining and biochemical analysis. To more completely identify the specific species of bacterium isolated and their role in the antibacterial activity isolated herein, the environmental specimens were further analyzed using restriction fragment length polymorphism (RFLP) analysis. RFLP analysis was used to differentiate the various species of Bacillus found within the plant as well as definitive identification of Aeromicrobioum species and Curtobacterium species.

The efficacy of aloe liquid (see e.g., Coats, *Aloe Vera: The Inside Story*) as an antimicrobial agent is shown herein to have a wide range of gram negative and gram positive bacteria. The antimicrobial agents of the present invention are shown herein to effectively kill, or greatly reduce or eliminate the growth rate of the following bacteria: *Staphylococcus aureus, Streptococcus pneumonia, Streptococcus pyogenes, Pseudomonas aeruginosa, E. coli, Propionibacterium acne, Helicobacter pylori,* and *Salmonella typhi.*

The anti-bacteriocidal activity demonstrated herein is not due to the preservatives used in the preparation of the clear gel or the isolation of the antibacterial components, as the antimicrobial agents isolated herein were isolatable from liquid collected directly from freshly cut whole leaves prior to used in the same killing assays.

In addition to the antimicrobial activities of its liquid, it also has been shown to be nontoxic even when taken internally. These properties combined provide the impetus for the use of the antimicrobial agents isolated herein when used alone or in combination. The present invention demonstrates the isolation and identification of new, non-toxic, FDA approved antimicrobial agents that have been identified and isolated from the Aloe plant. These agents are efficacious and nontoxic, with a broad spectrum of antimicrobial properties.

Generally, and in one form of the invention, a composition isolated from the gel liquid of *Aloe vera* including, at least one antimicrobial agent isolated from the clear gel isolated from the whole leaf of *Aloe vera,* wherein the antimicrobial agent is an agent produced by the *Aloe vera* or indigenous bacteria that colonize the *Aloe vera,* is disclosed.

Furthermore, a method of decreasing the growth of a broad spectrum of bacteria including the steps of, isolating at least one antibacterial agents from the clear gel of an *aloe vera* plant and directly contacting the bacteria with at least one antibacterial agent from *aloe vera,* is also disclosed.

The present invention is based on the recognition that *aloe vera* isolated have been used to treat, and increase the healing rate of, wounds and other infectious diseases. The present invention is also based on the recognition that antibacterial agents secreted by *aloe vera* and the bacteria that grow in the gel and rind of *aloe vera* and which exhibit a wide range antimicrobial activity when exposed directly to the target microbe can be isolated. The antibacterial agents isolated herein have molecular weights of about: 555,000; 470,000; 240,000; 160,000; 25,000 and 4,000 Daltons.

Also, the antibacterial agents isolated herein, are partially secreted by bacteria that grow in the gel and rind of *Aloe vera.* The secreted products of these species of bacteria exhibit a wide range antimicrobial activity when exposed directly to target microbes and each other and include: Aerobacterium, Bacillus, Curtobacterium, Arthrobacter, Sporosarcina, and Clavibacter.

BRIEF DESCRIPTION OF THE DRAWINGS

For a more complete understanding of the features and advantages of the present invention, reference is now made to the detailed description of the invention along with the accompanying FIGURE in which.

DETAILED DESCRIPTION OF THE INVENTION

Figure 1:
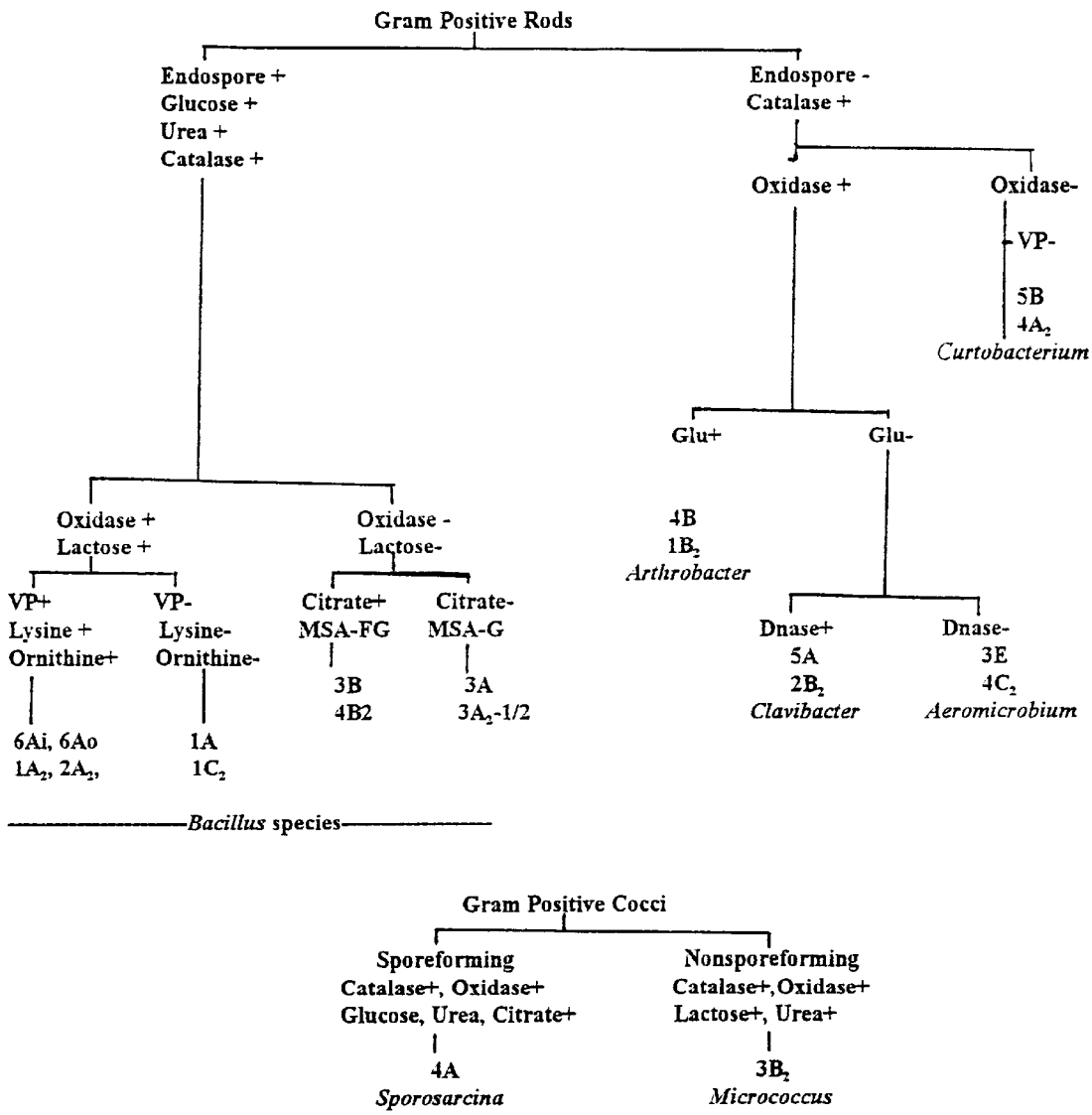
FIG. 1 is a taxonomic chart of the DNA fingerprint analysis of bacterial isolates according to the present invention.

While the making and using of various embodiments of the present invention are discussed in detail below, it should be appreciated that the present invention provides many applicable inventive concepts which can be embodied in a wide variety of specific contexts. The specific embodiments discussed herein are merely illustrative of specific ways to make and use the invention and do not delimit the scope of the invention.

Competition for nutrients and bacteriocin production play a role in determining the establishment of microbial communities in nature. When analyzing symbiotic associations between plants and bacteria, the presence of chemicals produced by the host as well as the bacteria play a role in the interaction. In the case of *Aloe vera barbedensis,* a tropical or subtropical plant of the genus Aloe. These plants are characterized by having lance shaped leaves that contain a viscous clear gel. The leaves are given structural rigidity by hairlike connective fibers. The clear gel of the *aloe vera* is to be distinguished from the thick, mucilaginous yellow juice that occurs about the base of the plant leaves and adjacent the rind of the leaf. This yellow juice, generally known as aloin, has been used for many years as an ingredient in many cathartics and purges.

The therapeutic qualities of the clear gel of *aloe vera* leaves depend to a large extent on the freshness of the gel. For example, the gel of the Aloe plant has been used to stop the pain caused by a jelly fish sting. If the gel has been exposed to air and light for about one and a half hours, however, the ability of the gel to reduce the concomitant immediate type hypersensitivity form of inflammation is greatly reduced.

The Aloe plant has been shown for centuries to exert broad spectrum of disease curing activities, these activities have not been characterized at the molecular biologic level. With the renewed interest in the isolation and characterization of antimicrobial agents, the present inventors recognized that in addition to the ability to promote the healing of animal cells, that Aloe gel may also contain antimicrobial agents.

Aloe Plant Antimicrobial Agents

A screen for antimicrobial activity of the aloe liquid was developed by the present inventors to quantify and qualify the antimicrobial activity of the aloe liquid. A number of strains of bacterial were tested. The following strains of Streptococci pneumoniae were obtained from the American Type Culture Collection: ATCC 51936, ATCC 51937, ATCC 51938, and ATCC 51422. Each of these has been implicated in severe cases of otitis media, and are multi-drug resistant (MDR). Culture of these microorganisms was on Brain Heart Infusion media (BHI) supplemented with 5% sheep red blood cells (SRBC). Incubation was under increased $CO_2$ conditions to enhance growth.

The organisms were initially grown overnight to log phase. Dilutions were made to obtain cultures of approximately $10^5$ cells/ml. These bacteria were inoculated into the appropriate media to which 90% aloe liquid (Coates Aloe International as well as freshly isolated) was added. The present inventors recognized that the aloe liquid is non-toxic to animals in pure form, be it topical or internal, therefore, studies can be conducted using pure aloe liquid isolated and sterile. Positive and negative controls were used to verify the grown and killing data, as well as the sterility of the components used. Proper sterile technique was used throughout these studies. Inoculations were conducted under a sterile hood or using standard bacteriologic techniques. The final concentration of cells in the aloe liquid cell culture, and control cultures, was $10^4$ cells/ml. Aliquots of the culture were sampled at 0, 6, 12, and 24 hours and plated onto BHI with 5% SRBC, without aloe liquid, to determine the number of viable cells remaining in the culture. The following data were collected (all counts represent the average of triplicate platings):

| STRAIN | TIME | | | |
|---|---|---|---|---|
| | 0 Hrs | 6 Hrs | 12 Hrs | 24 Hrs |
| ATCC 51936 | $5 \times 10^4$ | $3 \times 10^4$ | $1 \times 10^2$ | 0 |
| ATCC 51937 | $6 \times 10^4$ | $4 \times 10^4$ | $1 \times 10^2$ | 0 |
| ATCC 51938 | $5 \times 10^4$ | $4 \times 10^4$ | $8 \times 10^2$ | 0 |
| ATCC 51422 | $8 \times 10^4$ | $8 \times 10^4$ | $7 \times 10^2$ | 0 |

In addition to broth culture assays, diffusion plates were also used to assess the efficacy of the aloe liquid. BHI plates supplemented with 5% SRBC were swabbed with overnight cultures of one of the strains so that a lawn of growth would result upon overnight incubation. A well was cut into the center of each plate and filled with 100% aloe liquid (Coats Aloe International). The plates were incubated overnight and zones of inhibition measured the following day. Each of the strains of Streptococcus pneumoniae exhibited strong susceptibility to aloe liquid as evidences by rings of inhibition averaging 2 cm in diameter.

The results of the assays of antimicrobial activity on the bacterial strains Helicobacter pylori ATCC 49503 and Streptococcus pneumoniae ATCC 35088. The assays were run twice in triplicate and the percentages of killing activity compared to control cultures under the same conditions without aloe product added. All cultures contained 5% sheep red blood cells for survival of these bacterial strains and were incubated in atmospheres enriched in $CO_2$.

| % Aloe Product | Helicobacter pylori % Killing | Streptococcus pneumoniae % Killing |
|---|---|---|
| 90% | 33% at 6 hrs | 10% at 6 hrs |
| | 100% at 12 hrs | 80% at 12 hrs |
| | | 100% 18 hrs |
| 75% | 71% at 24 hrs | 43% at 24 hrs |
| 50% | 49% at 24 hrs | 12% at 24 hrs |
| 25% | 34% at 24 hrs | 9% at 24 hrs |

Source of the Aloe Bacteriocidal Activity

In order to more closely identify and isolate the source of antimicrobial activity produced and isolated from the Aloe plant, the present inventors have analyzed the population dynamics within the indigenous microflora of Aloe vera. Localization and characterization of specific microbial populations was assessed using both direct culture of dissected plant material and immunological detection within tissue sections. Relative size and population diversity were determined through direct culture. In situ hybridization using specific immunological detection techniques demonstrated that discrete populations of bacteria are located within, and are segregate into, specific plant structures.

Most bacterial identification is accomplished using standard staining and biochemical analysis. The identification of bacterial and other microbes in environmental specimens requires attention to the fact that many microorganisms that are closely related members of the same genus or extremely unique organisms may be isolated. Isolation methods are often inadequate providing only broad classification at best. Therefore, in an attempt to clarify the classification of indigenous bacteria from Aloe vera barbedensis, Restriction Fragment Length Polymorphism (RFLP) analysis was used to identify variations in the strains of bacteria isolated. RFLP analysis indicated that various species of Bacillus are associated with the Aloe plant, and also led to the definitive identification of Aeromicrobioum species and Curtobacterium species.

The efficacy of aloe liquid (prepared according to the Coats process, U.S. Pat. No. 5,356,811, incorporated herein by reference) was used as an antimicrobial agent. A clear aloe vera mixture is a mixture that is substantially aloin free, i.e. the aloin content is less than 1 ppm. Aloe liquid was shown to have antibacterial activity against a wide range of gram negative and gram positive bacteria. The aloe liquid produced by the Coats process, and isolated from whole leaf, was shown to effectively kill: Staphylococcus aureus, Streptococcus pneumonia, Streptococcus pyogenes, Pseudomonas aeruginosa, E. coli, Propionibacterium acne, Helicobacter pylori, and Salmonella typhi.

The bactericidal activity of the aloe liquid was not due to the preservatives used in the preparation of this product, as liquid was collected directly from freshly cut whole leaves used in the same killing assays, demonstrated identical results. The inventors recognized that one advantage to the use of aloe liquid as an antimicrobial agent is that it is nontoxic even when taken internally. New antimicrobial agent were identified and isolated from the aloe liquid are efficacious and nontoxic, with broad spectrum properties.

Aloe Bactericidal Activity is not from Previously Identified Components

Previously isolated and identified individual aloe products as antimicrobial products were studied to confirm that these compounds were not responsible for the anti-bacterial activity identified herein. Purified extracts of several known Aloe components were provided by Dr. I. Danhoff, including: Albarin, Awbarin, Anthraquinone, Aloin A, Aloin A & B, Aloe emodin, and Yellow sap components were tested in like assays. When used in culture killing assays, only Aloin A and Aloe emodin showed any inhibition of bacterial growth, however, neither were comparable to the percent killing achieved using liquid from the whole leaf.

Isolation of Novel Aloe Constituents as Antimicrobial Products

Fractionation of fresh aloe liquid from whole leaf was conducted using standard column chromatography on Sephacryl 300. The resulting fractions were collected, peaks combined, the components precipitated to concentrates assayed for antimicrobial activity. Fractions containing molecular weights of approximately 550,000; 470,000; 240,000; 160,000; 25,000; and 4,000 Daltons were found to have varying degrees of bactericidal or bacteriostatic activity.

When these fractions were analyzed using gel electrophoresis, they were found to be mixtures of 1 to 3 components, and are thus considered to be heterogenous mixtures of the same compound whose molecular weight might be affected by glycosylation or association with lipid moieties. Alternatively, the fractions may contain proteins that have undergone varying forms of degradation or cleavage during processing. One the other hand, these fractions might indicate that several different components were isolated.

Chromatographic Separation

A chromatographic separation gel to be used in the procedures of the present invention is a three dimensional network which has a random structure. Molecular sieve gels comprise cross-linked polymers that do not bind or react with the material being analyzed or separated. For gel filtration purposes, the gel material is generally uncharged. The space within the gel is filled with liquid and the liquid phase constitutes the majority of the gel volume. Materials commonly used in gel filtration columns include dextran, agarose and polyacrylamide.

Dextran is a polysaccharide composed of glucose residues and is commercially available under the name Sephadex (Pharmacia Fine Chemicals, Inc.). The beads are prepared with various degrees of cross-linking in order to separate different sized molecules by providing various pore sizes. Alkyl dextran is cross-linked with N,N'-methylenebisacrylamide to from Sephacryl-S300 which allows strong beads to be made that fractionate in larger ranges than Sephadex can achieve.

Polyacrylamide may also be used as a gel filtration medium. Polyacrylamide is a polymer of cross-linked acrylamide prepared with N,N'-methylenebisacrylamide as the cross-linking agent. Polyacrylamide is available in a variety of pore sizes from Bio-Rad Laboratories (USA) to be used for separation of different size particles.

The separation gel material swell in water and in a few organic solvents. Swelling is the process by which the pores become filled with liquid to be used as eluant. As the smaller molecules enter the pores, their progress through the gel is retarded relative to the larger molecules which do not enter the pores. This is the basis of the separation. The beads are available in various degrees of fineness to be used in different applications. The coarser the bead, the faster the flow and the poorer the resolution. Superfine is to be used for maximum resolution, but the flow is very slow. Fine is used for preparative work in large columns which require a faster flow rate. The coarser grades are for large preparations in which resolution is less important than time, or for separation of molecules with a large difference in molecular weights. For a discussion of gel chromatography, see Freifelder, Physical Biochemistry, Second Edition, pages 238–246, incorporated herein by reference.

The most preferred methods of gel filtration for use in the present invention are those using dextran gels, such as Sephadex, and those using dextran-polyacrylamide gels such as Sephacryl which are able to separate molecules in the 180 to 500 kiloDalton range.

In addition studies, the fractions were compared singly and in various combinations in the bacterial killing assay. The level of killing achieved with whole aloe liquid could only be achieved when all the fractions were combined, indicating that the unconcentrated components together provide for aloe's broad spectrum antibacterial activity.

In order to more closely identify the components responsible for the broad spectrum antimicrobial activity observed for aloe liquid, and having isolated bacteria indigenous to the aloe plant, the present inventors recognized that the bacteria might be the source of some or all of the broad spectrum antimicrobial activity identified herein.

Eight distinct microorganisms were repeatedly been isolated from the rind and gel of the Aloe plant. Population studies have indicated the relative abundance and locale of each of these representatives. Since many antimicrobial substances are known to be produced by other bacteria, the production of such bacteriocins from each aloe isolate was analyzed. Three bacteria produced secretable products that were capable of killing one or more of the following indicator organisms, including: *Staphylococcus aureus, E. coli, Pseudomonas aeruginosa,* and Enterococcus (Streptococcus) *faecalis.*

Using gel electrophoresis, comparison of the secreted products and whole aloe liquid, three bands appear to be shared. Those of molecular weight 470,000; 160,000; and 25,000. Using antibody staining techniques, two of the bacteria displaying antimicrobial activity were localized within the rind of the plant; one at the gel rind interface, the other just below the outer cuticle of the plant, and within the parenchymal tissue. The distinct locations of the bacteria were identified by the present inventors to be in prime locations for the products secreted by the bacteria to enter the veins of the plant and become constituents of the plant liquid along with those of plant origin.

Contributions from these bacteriocins provide part of the answer for the broad spectrum activity of the aloe liquid isolated from the whole leaf. None of the bacteriocins, alone or in combination, were capable of killing all of individually killing the microbes previously shown to be affected. The secreted products of the individual bacteria contribute some of the components identified in the fractionation studies, but not all.

Aloe Plant Defense Proteins Capable of Antimicrobial Activity

As the bacterial secretion products did not fully explain the plants full antimicrobial activity, mixed fractions, rather than clean single component fractions, were studied. Plant defense proteins appear to make up, or be responsible for, the last anti-bacterial components.

Most bacterial identification is accomplished using standard staining and biochemical analysis. In the identification of environmental specimens, where many microorganisms are closely related members of the same genus or extremely unique organisms, these methods are often inadequate providing only broad classifications at best. To further the classification of indigenous bacteria from *Aloe vera* previously isolated, RFLP (Restriction Fragment Length Polymorphism) analysis was initiated. These results have been helpful in differentiating the various species of Bacillus found within the plant as well as assisting in the identification of Aeromicrobium, Curtobacterium, and Clavibacter isolates.

Microbiologists have historically relied on cultural and biochemical analysis for the identification of microorganisms. While this provides adequate information for classification to the genus and sometimes species level, it lacks the sensitivity required to detect strain variations in many groups of bacteria. Such identifications are of particular importance when dealing with environmental samples where selection pressures favor subtle variations within species. Both morphological and biochemical characters are often strongly influenced by the environment, and thus special procedures are required to distinguish genotypes from phenotypic variations.

Using standard bacteriological procedures, a variety of bacteria were isolated from two different Aloe vera plants. These isolates were identified to species level. Representatives of the genus Clavibacter, Curtobacterium, and Arthrobacter (established plant symbiotes) and multiple members of the genus Bacillus comprised the majority of the indigenous flora. There are over 100 different species of Bacillus established in Bergey's Manual of Systemic Bacteriology (many with minor biochemical variations). Clavibacter and Curtobacterium were originally placed in the genus Corynebacterium, but have been separated based on rRNA patterns. Because the members of these groups are biochemically similar, DNA fingerprinting was used to provide more definitive classification information including DNA polymorphisms.

Materials and Methods

PLANTS. Aloe vera plants were obtained from two sources: Coats Aloe International (Mexico) and Calloway Nurseries (Texas). Additional work was also conducted on a plant from Irving, Tex. (original origin unknown) with similar results. The plants were maintained in the Haggerty Science building on the University of Dallas campus. Natural light exposure was obtained by placing the plants in a hallway floor to ceiling window on the east side of the building. Temperatures were maintained around 25° C. Plants were watered weekly or as needed, allowing the soil to dry in between.

MICROBIAL ISOLATION. Leaves were cut at the base near the stalk with a sterile scalpel. They were they washed with soap (Dial Antibacterial Soap) to remove surface contaminants, rinsed throughly with sterile water followed by a rinse with 70% ethanol, and allowed to air dry under a sterile hood. Gloves were used through out the isolation process to prevent possible contamination from other sources.

The leaves were cut into strips and finely minced in preparation for tissue homogenization. One gram of plant tissue was suspended in 2 mls of sterile saline and homogenized (Dounce vessel). The resultant suspension was plated using serial dilutions onto Tryptic Soy Agar. Plates were incubated at 37° C., and inspected for growth at 24 and 48 hours. Pure cultures were established from the individual, distinctive colonies which grew from the suspension.

MORPHOLOGICAL AND BIOCHEMICAL CHARACTERIZATION. Gram stains and acid fast stains were done on 18 hour cultures. The spore stains were done on five day cultures. Standard microbiological media (Difco and BBL) and formulations thereof, were used to determine both morphological and biochemical characteristics. Enterotubes in place of individual tube media for some of the assays. Resulting data was used in the classification of the various isolates using Bergey's Manual of Determinative Bacteriology.

ISOLATION OF DNA. Cultures were grown overnight at 37° C. in 30 ml Tryptic Soy Broth. Cells were collected by centrifugation, resuspended and lysed in 0.2 M glucose with lysozyme (10 ug/ml) and subsequently digested with proteinase K. Proteins, carbohydrates, and lipids were removed from the suspension by phenol:chloroform:Isoamyl Alcohol extraction. DNA was precipitated by addition of cold 95% ethanol at −20° C. The recovered DNA was resuspended in sterile Tris-EDTA buffer and contaminating RNA removed by overnight digestion with RNAse. This was followed by a second proteinase K digestion, phenol:chloroform:Isoamyl alcohol extraction and ethanol precipitation. Purified DNA was quantified spectrophotometrically.

DNA FINGERPRINTING. Five to 10 ug of DNA was completely digested with restriction enzymes (Promega) under the recommended conditions. Restriction fragments were separated from each other by electrophoresis on horizontal agarose gels using 1% in Tris:Acetate:EDTA buffer. Hind III digested phage lambda fragments were used as molecular weight markers. Digestion patterns were compared and used as additional classification information.

Morphological and Biochemical Characterization

A total of 20 bacterial cultures isolated from two separate Aloe vera plants. Each was assayed using standard biochemical media. Isolates were tentatively placed in a specific genus according to Bergey's Manual of Determinative Bacteriology.

Of the ten isolates from each plant, five from each of the two plants were classified as members of the genus Bacillus. These isolates were gram positive spore forming rods which were catalase positive. Minor variations in sugar utilization and exoenzyme production demonstrated a wide variety of species present within the plants. Two isolates which were catalase negative were also classed as members of the Bacillus genus due to other biochemical reactions. Catalase positive non-spore forming irregular rods which were oxidase negative represented members of Curtobacterium. Those which were oxidase positive isolates represented members of Clavibacter, Arthrobacter, or Aeromicrobium. All bacteria in these groups exhibited pleomorphic morphology, some with distinct rod-cocci cycle. Catalase negative nonendospore formers were placed in the genus Listeria. Only a few cocci were isolated; all were gram positive. One sporeformer was isolated from Plant 1 and was classed as Sporosarcina. The remaining cocci were catalase positive nonsporeformers and were placed in the genus Micrococcus.

DNA Fingerprinting Analysis

FIG. 1 is a taxonomic analysis and chart that was developed using DNA fingerprint analysis and biochemical testing of the isolates. Both gram positive rods and gram positive cocci were identified using gram staining followed by biochemical and DNA fingerprint analysis. The isolates identified included members of the Bacillus, Arthrobacter, Curtobacterium, Clavibacter, Aeromicrobium, Sporosarcina and Micrococcus species.

TABLE 3

BIOCHEMICAL CHARACTERISTICS

| | ISOLATES | | | | | | | | | |
|---|---|---|---|---|---|---|---|---|---|---|
| Characteristics | 1AI | 3A | 3B | 3E | 4A | 4B | 5A | 5B | 6Ai | 6Ao |
| Gram Stain | + | + | + | + | + | + | + | + | + | + |
| Morphology | R | R | R | R | C | P | R | P | P | R |
| Spore | + | + | + | − | + | − | − | − | + | + |
| Catalase | + | + | + | Sl | + | + | + | + | + | + |
| Oxidase | + | − | − | + | − | + | + | − | + | + |
| Glucose | + | + | + | Sl | + | + | − | + | + | + |
| Lactose | Sl | − | Sl | − | Sl | + | + | − | + | + |
| Arabinose | + | − | Sl | − | + | + | − | − | Sl | + |

TABLE 3-continued

BIOCHEMICAL CHARACTERISTICS

| | ISOLATES | | | | | | | | | |
|---|---|---|---|---|---|---|---|---|---|---|
| Characteristics | 1AI | 3A | 3B | 3E | 4A | 4B | 5A | 5B | 6Ai | 6Ao |
| Adonitol | + | − | Sl | + | − | + | + | + | + | + |
| Sorbitol | − | − | + | − | − | − | − | − | Sl | − |
| Lysine | − | − | Sl | Sl | − | − | + | + | + | + |
| Ornithine | − | − | Sl | Sl | − | − | + | + | + | + |
| Indole | − | − | − | − | − | − | − | − | − | − |
| Citrate | + | − | + | − | + | + | + | + | + | + |
| Urea | + | + | + | + | + | + | + | + | + | + |
| VP | − | + | + | − | − | − | − | − | + | + |
| Nitrate | + | + | + | + | + | + | − | − | + | + |
| Starch | + | + | + | − | + | + | − | − | + | + |
| DNAse | + | − | + | + | + | + | + | − | + | + |
| MSA | − | G | FG | − | G | G | − | G | FG | FG |

***R—bacilli,
C—cocci,
P—pleomorphic,
Sl—slight reaction,
G—growth,
FG—fermentative growth Population Dynamics Among Indigenous Microflora Isolated from *Aloe Vera*

Both competition for nutrients and bacteriocin production play a role in determining the establishment of microbial communities. Symbiotic associations may be influenced by the presence of plant defense compounds produced by the host. In the case of *Aloe vera*, the plant has shown to secret many anthraquinones (produced by a large number of plants), which have been shown to effectively kill microorganisms. Studies were conducted to determine the population dynamics within the indigenous microflora of *Aloe vera*. The localization of specific microbial populations was assessed using both direct culture of dissected plant material and immunological detection within tissue sections. Relative size and population diversity were determined through direct culture while the immunological detection demonstrated discrete populations within specific plant structures.

Isolation revealed ten different microorganisms indigenous to the Aloe plant. These studies were concentrated on determining the population dynamics of the ten isolates. Comparative numbers of the microorganisms at different levels within the plant were first determined using standard bacteriological plating techniques. Microbial interactions were examined using spot plates to determine competition and tissue printing to determine the exact location within the plate of each of the microorganisms.

MICROBIAL ISOLATION. Leaves were cut at the base near the stalk with a sterile scalpel. They were they washed with soap (Dial Antibacterial Soap) to remove surface contaminants, rinsed throughly with sterile water followed by a rinse with 70% ethanol, and allowed to air dry under a sterile hood. Gloves were used through out the isolation process to prevent possible contamination from other sources.

The leaves were cut into three segments: top, middle, and bottom. Each of there were processed separately. The segments were cut into strips then finely minced in preparation for tissue homogenization. In addition, the rind was separated from the internal 'gel' of the plant for some strips in each segment and processed. One gram of plant tissue was suspended in 2 mls of sterile saline and homogenized (Dounce vessel). The resultant suspensions were plated using serial dilutions onto Tryptic Soy Agar. Plates were incubated at 37° C., and inspected for growth at 24 and 48 hours.

POPULATION ENUMERATION. The number of similar colonies from each of the suspension was counted and recorded.

SPOT PLATES. Overnight cultures of each of the isolates were swabbed onto Tryptic Soy Agar (TSA) plates to produce a lawn of growth. The growth of each of these was challenged by spotting the other symbiotes on top of the lawn and allowing the organisms to grow overnight at 37° C. A clear area around the spot indicated exclusive competition between the two organisms. A zone of inhibition which appeared to have been there initially but had been filled in at a later time was interpreted as a static competition, where increasing population levels over came the initial exclusion.

TISSUE PRINTING. Leaves from the plants were cut and cleaned as for the homogenization procedure. They were then cut into strips approximately 5 mm in length. These were placed onto nitrocellulose filters and pressure was applied to facilitate the transfer of bacteria from the plant tissue onto the filter. The filters were either used immediately or stored dry at −4° C.

ANTIBODY PREPARATION. Cultures of each of the microorganisms were grown up overnight in 10 mls of Tryptic Soy Broth. The cells were pelleted, resuspended in 1 ml of saline, and heated at 70° C. for 1 hour to inactivate the cells. Further inactivation was achieved by addition of formaldehyde to the cells at a concentration of 0.6%. Inactivation was checked by plating both aerobically and anaerobically for 48 hours. No growth indicated complete inactivation.

Lowry protein assays were done to determine the antigen concentration. Two hundred micrograms ($\mu$g) of antigen was administered to Sprague Dawley rats in the presence of complete Freund's adjuvant. The second administration of antigen was fourteen days later in the presence of incomplete Freund's adjuvant. The rats were bled ten days later and the serum isolated. Antibodies were purified using hydoxyapatite.

IMMUNOBLOTTING. The tissue blots were blocked with Phosphate Buffered Saline (PBS) containing skim milk. Primary antibody was applied to the blot for 1 hour. Subsequent washings with PBS removed unbound antibody. Second antibody (anti-rat IgG-peroxidase) was applied for 1 hour. Unbound second antibody was washed off and the peroxidase substrate 4-chloro-1-napthol was used to stain the blot. Areas of intense blue-black indicated areas of microbial localization.

TABLE 4

POPULATION ENUMERATION

| SECTION/ | MICROORGANISM (per 50 ug tissue) | | | | | | | | | | |
|---|---|---|---|---|---|---|---|---|---|---|---|
| SITE | 1 | 2 | 3 | 4 | 5 | 6 | 7 | 8 | 9 | 10 | Total |
| Bottom-Whole | 1 | 15 | 1.5 | 9 | 58 | 1 | 0 | 0 | 0 | 0 | 84.5 |
| Bottom-Gel | 0 | 0 | 0 | 40 | 0 | 0 | 1 | 0 | 300 | 0 | 340 |
| Bottom-Rind | 2.5 | 19 | 1 | 4 | 61 | 0 | 0 | 1 | 0 | 0 | 87.5 |
| Mid-Whole | 2.5 | 21 | 1 | 2.5 | 0 | 3.5 | 1 | 0 | 0 | 1 | 1.5 |
| Mid-Gel | 0 | 0 | 0 | 41 | 0 | 0 | 0 | 0 | 500 | 0 | 541 |
| Mid-Rind | 6 | 24 | 2 | 1 | 0 | 4 | 1 | 0 | 0 | 1 | 39 |
| Top-Whole | 1.5 | 13 | 2.5 | 0 | 35 | 3 | 1 | 20 | 0 | 1 | 77 |
| Top-Gel | 4 | 19 | 1.5 | 0 | 0 | 2.5 | 0 | 0 | 0 | 5 | 32 |
| Top-Rind | 1 | 25 | 2 | 1 | 25 | 15.5 | 1 | 21 | 0 | 1 | 95.5 |

Microbial Key
1 - Aeromicrobium - 3E
2 - Bacillus - 3A

TABLE 4-continued

POPULATION ENUMERATION

| SECTION/ SITE | MICROORGANISM (per 50 ug tissue) | | | | | | | | | | |
|---|---|---|---|---|---|---|---|---|---|---|---|
| | 1 | 2 | 3 | 4 | 5 | 6 | 7 | 8 | 9 | 10 | Total |

3 - Bacillus - 6Ai
4 - Curtobacterium - 5B
5 - Arthrobacter - 4B
6 - Bacillus - 3B
7 - Bacillus - 1A
8 - Sporosarcina - 4A
9 - Clavibacter - 5A
10 - Bacillus - 6Ao

TABLE 5

MICROBIAL COMPETITION

| LAWN | SPOT ISOLATE | | | | | | | | | |
|---|---|---|---|---|---|---|---|---|---|---|
| | 1A | 3A | 3B | 3E | 4A | 4B | 5A | 5B | 6Ai | 6Ao |
| 1A |  | + | ++ | + | ++ | ++ | ++ | - | ++ | - |
| 3A | - |  | - | - | -/+ | - | -/+ | - | - | -/+ |
| 3B | - | - |  | - | - | - | - | - | - | +/- |
| 3E | - | - | + |  | ++ | - | ++ | - | ++ | - |
| 4A | - | - | - | - |  | - | - | - | - | - |
| 4B | - | - | ++ | - | ++ |  | ++ | - | ++ | - |
| 5A | - | - | - | -/+ | - | - |  | - | - | - |
| 5B | Not Available | | | | | | | | | |
| 6Ai | - | - | - | - | - | - | - | - |  | - |
| 6Ao | - | +/- | ++ | +/- | ++ | - | ++ | - | ++ |  |

Microbial Key
1A - Bacillus
3A - Bacillus
3B - Bacillus
3E - Aeromicrobium
4A - Sporosarcina/Micrococcus
4B - Arthrobacter
SA - Clavibacter
5B - Curtobacterium
6Ai - Bacillus
6Ao - Bacillus
Growth Key
+ = mild inhibition
++ = strong inhibition
-/+ = static inhibition
- = no inhibition Representatives of all the isolates except Clavibacter were found present within the rind. Clavibacter dominated the gel region. A few Bacillus species, Aeromicrobium and Curtobacterium species were found in low numbers within the gel. The majority of the isolates were associated with or immediately surrounding the tubule containing rind (Table 4). On the surface this result is surprising since the rind is the site of yellow sap, comprised primarily of anthraquinones. These compounds have been classified as plant defense compounds. They are also extremely unstable. Not only are anthraquinones readily inactivated through oxidation, it is conceivable that many of the Bacillus species present within the rind secrete enzymes which might assist their inactivation. One of the characteristics of Bacillus species is the prolific secretion of a wide variety of exoenzymes.

Location in the rind/tubules may also be a protective measure by those microorganisms sensitive to some bacteriocin produced by Clavibacter and thus reflect competitive exclusion between endosymbiotes. A review of population numbers reveals that although the variety of microbes is small within the gel fillet, the population density of those found in the gel is at least five times more dense than even the most prominent member of the rind microenvironment (Table 4). Members of the rind population, specifically Aeromicrobium, do show inhibitory activity against the gel isolates (Table 5). These organisms could establish the barrier between the rind and the secretions of the gel allowing the various rind organisms to live undisturbed.

Bacteria are known to produce substances known as bacteriocins which are capable of killing closely related species, a process termed competitive exclusion. The data show that various members of the indigenous microflora do produce bacteriocins setting up regions of exclusive regions within the plant.

Because of the possibility that these bacteriocins interfered with the identification of certain microorganisms within the gel and rind, immunoblotting of tissue prints was chosen as a more specific method for localization of the plant's microflora. Only four microorganisms have successfully been localized using this method. The inability to develop antibodies may be due either to low antigenic properties of the remaining microorganisms or to the low population numbers within the plant itself making it difficult to transfer sufficient numbers required for immunoblots techniques.

Bacillus 1A shows distinctive localization within the inner tubules of the rind while Bacillus 6Ai and 3B appear to inhabit the more exterior regions, even outside of the plant itself in the skin. These results place the sporeforming coccus Sporosarcina (4A) at the interface between the rind and the gel and within the gel itself. These results confirm the population enumeration studies.

A wide range of bacteria are adapted to various microenvironments at the soil and air interface and are important in nutrient uptake, frost damage, and biological control of plant pathogens. There are also those associated with the plant surfaces, both root and aerial. The location of these organisms reflects their ecology. Physiologically some may be extracellular, multiplying within intercellular spaces but not penetrating plant cell walls or entering protoplasts. Others may be able to penetrate the higher plant cell. These associations ultimately lead to symbiotic interactions: commensalistic, mutualistic, or in some instances parasitic. Parasitic conditions, however, are considered to be rare with respect to plant-bacteria associations. The internal environment of healthy plants is not conducive to bacterial growth in general, however, the acquisition and development of cell wall degrading enzymes and toxins leading to disease. Alternatively, the secretion of compounds with the ability to inhibit plant defense compounds may assist in the establishment of certain symbioses.

Aqueous compositions (inocula) of the bacteriocins isolated from the Aloe plane as described herein, comprise an effective amount of the antimicrobial agent dissolved or dispersed in a pharmaceutically acceptable aqueous medium. As used herein the terms "contact", "contacted", and "contacting", are used to describe the process by which an effective amount of a pharmacological agent, e.g., pure or dilute aloe gel, comes is direct juxtaposition with the target cell. The phrase "pharmaceutically acceptable" refers to molecular entities and compositions that do not produce an allergic or similar untoward reaction when administered to a human, such as the gel isolated for *Aloe vera* as described herein.

The preparation of an aqueous composition that contains a protein or proteoglycan, such as the active components derived from the bacteria and aloe plant, is well understood in the art. Typically, such compositions are prepared as injectables, either as liquid solutions or suspensions; solid forms suitable for solution in, or suspension in, liquid prior to injection can also be prepared. The preparation can also be emulsified.

Proteoglycans, for example, can be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like.

For parenteral administration in an aqueous solution, for example, the aloe liquid or gel can be used directly without any toxic effects to the animal. Alternatively, the aloe solution and the antimicrobial agents identified herein, can be dissolved or resuspended, in a suitable buffer, if necessary. Liquid diluents can first be rendered isotonic with sufficient saline or glucose.

To kill a cell in accordance with the present invention, one would generally contact the cell with pure or diluted aloe gel in a combined amount effective to kill the microbial cell. The term "in a combined amount effective to kill the cell" means that the amount of bacteriocins are sufficient so that, when combined within the cell, the cell is induced to undergo apoptosis or another form of cell death. Although not required in all embodiments, the combined effective amount of the isolated aloe gel compounds will preferably be an amount that induces significantly more cell death than the use of either element alone, and most preferably, the combined effective amount will be an amount that induces synergistic cell death in comparison to the effects observed using either element alone.

While these particular aqueous solutions are especially suitable for intravenous, intramuscular, subcutaneous and intraperitoneal administration, the aloe solution of the present invention can be administered directly at full concentration. In this connection, sterile aqueous procedures to produce aloe gel can be employed, as will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

While this invention has been described in reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

REFERENCES

Coats, B. 1995 *Aloe Vera: The Inside Story*, Coats.
Harlow E and Lane D. 1988. *Antibodies: A Laboratory Manual*, Cold Spring Harbor Press.
Holt C A. 1992. Detection and localization of plant pathogens, *Tissue Printing*. Reid PD, et al, editors. Academic Press.
Reid P D. 1992. Physical Tissue Printing. In: *Tissue Printing*, Reid P D, et al, editors. Academic Press.

What is claimed is:

1. A composition derived from a clear *aloe vera* mixture which has less than 1 ppm aloin content and which has been prepared from *aloe vera* gel, consisting essentially of a fraction obtained by gel filtration of said clear mixture, wherein the fraction has an average molecular weight of approximately 550,000 Daltons and has bactericidal or bacteriostatic activity.

2. A composition derived from a clear *aloe vera* mixture which has less than 1 ppm aloin content and which has been prepared from *aloe vera* gel, consisting essentially of a fraction obtained by gel filtration of said clear mixture, wherein the fraction has an average molecular weight of approximately 470,000 Daltons and has bactericidal or bacteriostatic activity.

3. A composition derived from a clear *aloe vera* mixture which has less than 1 ppm aloin content and which has been prepared from *aloe vera* gel, consisting essentially of a fraction obtained by gel filtration of said clear mixture, wherein the fraction has an average molecular weight of approximately 240,000 Daltons and has bactericidal or bacteriostatic activity.

4. A composition derived from a clear *aloe vera* mixture which has less than 1 ppm aloin content and which has been prepared from *aloe vera* gel, consisting essentially of a fraction obtained by gel filtration of said clear mixture, wherein the fraction has an average molecular weight of approximately 160,000 Daltons and has bactericidal or bacteriostatic activity.

5. A composition derived from a clear *aloe vera* mixture which has less than 1 ppm aloin content and which has been prepared from *aloe vera* gel, consisting essentially of a fraction obtained by gel filtration of said clear mixture, wherein the fraction has an average molecular weight of approximately 25,000 Daltons and has bactericidal or bacteriostatic activity.

6. A composition derived from a clear *aloe vera* mixture which has less than 1 ppm aloin content and which has been prepared from *aloe vera* gel, consisting essentially of a fraction obtained by gel filtration of said clear mixture, wherein the fraction has an average molecular weight of approximately 4,000 Daltons and has bactericidal or bacteriostatic activity.

7. A method of decreasing the growth of a bacteria comprising: preparing a composition derived from a clear *aloe vera* mixture which has less than 1 ppm aloin content and which has been prepared from *aloe vera* gel, consisting essentially of one fraction obtained by gel filtration of said clear mixture, wherein the fraction has an average molecular weight of either approximately 550,000 or 470,000 or 160,000 or 25,000 or 4,000 Daltons and contacting said bacteria with said fraction.

* * * * *